United States Patent
Karasawa

(10) Patent No.: US 7,481,769 B2
(45) Date of Patent: Jan. 27, 2009

(54) ULTRASONIC DIAGNOSING APPARATUS

(75) Inventor: Hiroyuki Karasawa, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 711 days.

(21) Appl. No.: 10/944,800

(22) Filed: Sep. 21, 2004

(65) Prior Publication Data

US 2005/0070795 A1    Mar. 31, 2005

(30) Foreign Application Priority Data

Sep. 30, 2003    (JP)    ............... 2003-339004

(51) Int. Cl.
*A61B 8/00*    (2006.01)
(52) U.S. Cl. .................. 600/443; 600/437; 600/442
(58) Field of Classification Search ................ 600/437, 600/443, 442
See application file for complete search history.

(56) References Cited

U.S. PATENT DOCUMENTS

| | | | |
|---|---|---|---|
| 4,414,850 A * | 11/1983 | Miwa et al. ........... | 73/599 |
| 4,452,082 A * | 6/1984 | Miwa ................... | 73/599 |
| 4,509,524 A * | 4/1985 | Miwa ................... | 600/437 |
| 4,511,984 A * | 4/1985 | Sumino et al. ......... | 600/437 |
| 4,575,799 A * | 3/1986 | Miwa et al. ........... | 600/442 |
| 4,723,553 A * | 2/1988 | Miwa et al. ........... | 600/442 |
| 4,858,124 A * | 8/1989 | Lizzi et al. ............ | 600/443 |
| 5,361,767 A * | 11/1994 | Yukov ................. | 600/442 |
| 5,417,215 A * | 5/1995 | Evans et al. ........... | 600/442 |
| 5,746,209 A * | 5/1998 | Yost et al. ............ | 600/453 |

FOREIGN PATENT DOCUMENTS

| | | |
|---|---|---|
| JP | 05-042147 A | 2/1993 |
| JP | 10-179589 A | 7/1998 |
| JP | 2000-005180 A | 1/2000 |
| JP | 2001-170046 A | 6/2001 |

OTHER PUBLICATIONS

Lizzi. F.L., Laviola, M.A., and Coleman, D.J., Tissue Signature Characterizatoin Utilizing Frequency Domain Analysis, 1976 Ultrasoics Symposium, pp. 714-719.*

* cited by examiner

*Primary Examiner*—Brian L. Casler
*Assistant Examiner*—John F Ramirez
(74) *Attorney, Agent, or Firm*—Sughrue Mion, PLLC

(57) ABSTRACT

An ultrasonic diagnosing apparatus capable of improving an SN ratio and emphatically displaying characteristic tissues by acquiring information unique to tissues such as organs, bones, etc. in a living body. The ultrasonic diagnosing apparatus includes: a B-mode image data generating unit for generating first image data based on intensity of detection signals obtained by transmitting and receiving ultrasonic waves having a plurality of frequency components; a frequency component extracting unit for extracting at least one frequency component from the detection signals; a frequency image data generating unit for generating second image data based on intensity of the extracted at least one frequency component; and an image selecting unit for selecting at least one of the first image data and the second image data.

13 Claims, 6 Drawing Sheets

SPINE SECTION A

SOFT TISSUE (MUSCLE)
HARD TISSUE (BONE)

SOFT TISSUE (MUSCLE)
HARD TISSUE (BONE)

SOFT TISSUE (MUSCLE)
HARD TISSUE (BONE)

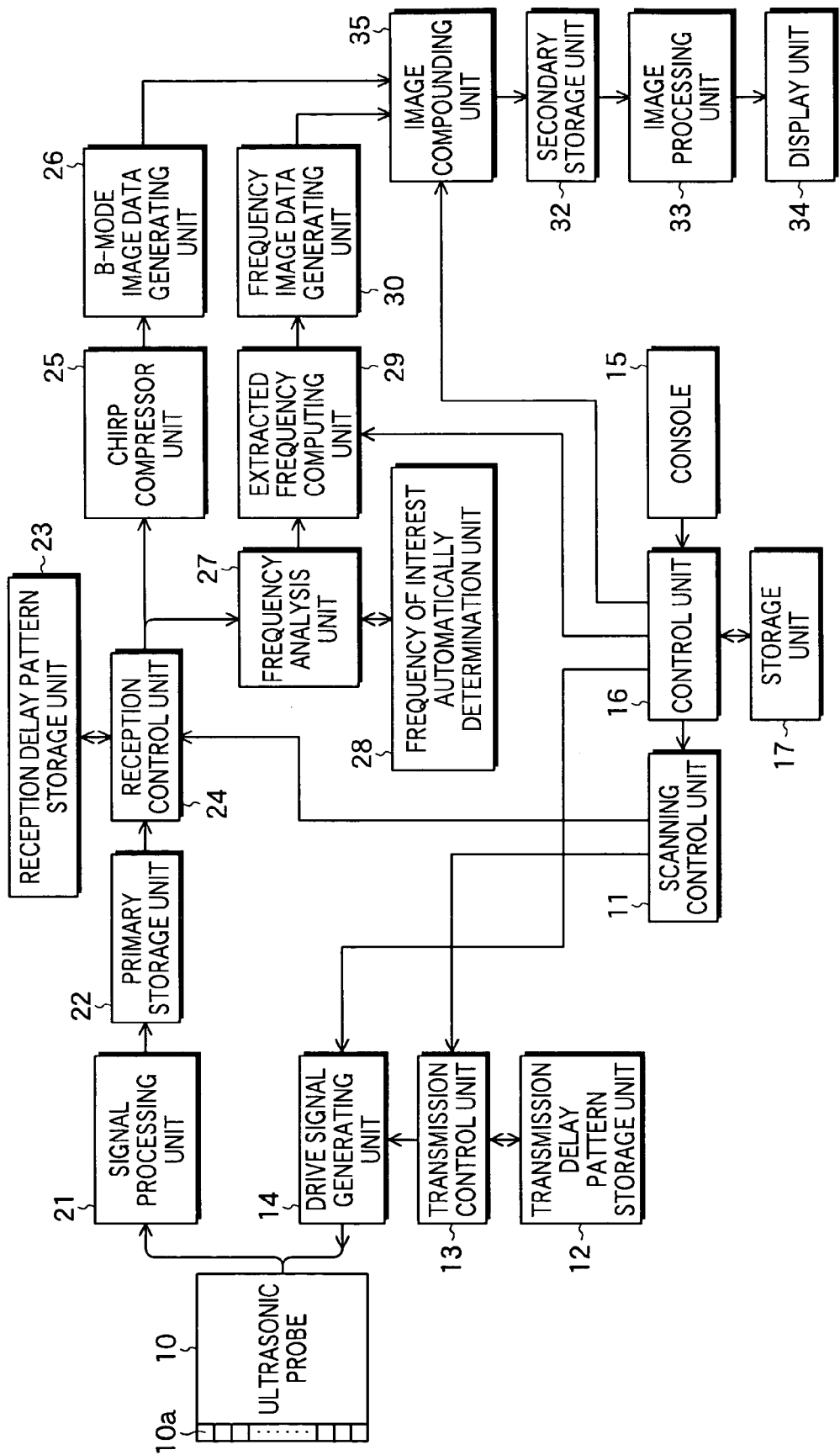

ULTRASONIC DIAGNOSING APPARATUS

BACKGROUND OF THE INVENTION

1. Field of the Invention

The present invention relates to an ultrasonic diagnosing apparatus for imaging organs, bones, etc. within a living body by transmitting and receiving ultrasonic waves to generate ultrasonic images to be used for diagnosis.

2. Description of a Related Art

In an ultrasonic diagnosing apparatus to be used for medical application, normally, an ultrasonic probe including plural ultrasonic transducers having transmitting and receiving functions of ultrasonic waves is used. By using such ultrasonic probe, an object to be inspected is scanned by an ultrasonic beam formed by compounding the plural ultrasonic waves and the ultrasonic echoes reflected inside the object are received, and thereby, image information on the object is obtained based on the intensity of the ultrasonic echoes. Furthermore, two-dimensional or three-dimensional images of the object are reproduced based on the image information.

By the way, when ultrasonic beams are transmitted from the ultrasonic probe to the human body, the amplitudes of the ultrasonic echoes reflected at the interfaces between soft tissues such as muscles and hard tissues such as bones become large, and therefore, these interfaces are displayed in high brightness in an ultrasonic image. On the other hand, because the ultrasonic echoes from inside and behind the hard tissues are weak, it is extremely difficult to visually recognize the image of the hard tissues such as bones, tendons, nucleus pulposus, etc. while separating those from the soft tissues such as muscles.

As a related technology, Japanese Patent Application Publication JP-P2001-170046A discloses a living tissue property diagnosing apparatus arranged so as to perform an accurate diagnosis regardless of a target of measurement. In the living tissue property diagnosing apparatus, signal analysis means includes pulse width setting means for setting a signal pulse width of an electric signal obtained from a received ultrasonic pulse, region extracting means for extracting plural regions of signal that are different from each other at least in parts of the regions from the range of the set signal pulse width, waveform characteristic value calculating means for calculating a predetermined waveform characteristic value in each of the extracted regions, difference computing means for computing the difference between the calculated waveform characteristic values, and corresponding time determination means for relating a result of the difference computation to a position of the living tissue from which the ultrasonic pulse has been generated by relating the result of the difference computation to a reception time of the ultrasonic pulse. As the waveform characteristic values, peak frequencies, center frequencies, bandwidth ratios, 6dB-reduced frequencies, primary moment, secondary moment, etc. are used. However, extracting plural regions of signal that are different from each other at least in parts of the regions from the range of the set signal pulse width corresponds to utilizing the difference between information in a depth direction within the object, and therefore, axial resolution is degraded. That is, differential characteristics in the depth direction are obtained and it cannot be a characteristic indicating a feature at one point.

Further, Japanese Patent Application Publication JP-P2000-5180A discloses an acoustic impedance measurement apparatus that is practicable and capable of displaying an acoustic impedance of a target of measurement in images with high resolution at high speed. This acoustic impedance measurement apparatus includes frequency converter means for obtaining frequency characteristics of ultrasonic reply signals, parameter extracting means for extracting a predetermined parameter from the frequency characteristics, and acoustic impedance calculating means for calculating the acoustic impedance of the target of measurement by using the extracted parameter. In the acoustic impedance measurement apparatus, in order to measure the acoustic impedance of the target of measurement, broadband pulse signals such as trapezoidal pulses and rectangular pulses are used. Such pulse signals are broadband, but include only unique frequency components determined depending on their own waveforms and the ratio between the components are limited.

Furthermore, Japanese Patent Application Publication JP-A-5-42147 discloses a lithotrity degree measurement apparatus in calculus spallation treatment within a living body for performing treatment with shockwave while observing the lithotrity condition as image information. This lithotrity degree measurement apparatus includes means for obtaining an amplitude value by converting received reflection waves into an electric signal, means for outputting a maximum amplitude value from the amplitude value of the electric signal, means for converting the signal into a frequency signal by performing frequency analysis of the electric signal, means for comparing the maximum amplitude value with a preset amplitude value, and means for calculating a predetermined characteristic value from the frequency signal if the comparing means judges that the maximum amplitude value is larger than the preset amplitude value. However, the information obtained by the apparatus is only the lithotrity degree and information on the tissues within the living body cannot be obtained.

Further, Japanese Patent Application Publication JP-A-10-179589 discloses ultrasonic image processing method and apparatus for performing image processing on tissues and body fluids on the basis of response frequencies which are different from the transmitting frequencies, specifically, harmonic echoes of the transmitting fundamental frequency and come back from the tissues or body fluids. However, such harmonic echoes are not necessarily generated from any tissue at sufficient amplitudes, and, although the harmonic echoes generated in the tissues are received, linear frequency response characteristics of the tissues are not thereby obtained.

SUMMARY OF THE INVENTION

The present invention has been achieved in view of the above-described problems. An object of the present invention is to provide an ultrasonic diagnosing apparatus capable of improving an SN ratio and emphatically displaying a characteristic tissue by acquiring unique information of organs, bones, etc. within a living body.

In order to solve the above-described problems, an ultrasonic diagnosing apparatus according to a first aspect of the present invention includes: first image data generating means for generating first image data on an object to be inspected based on intensity of detection signals obtained by transmitting ultrasonic waves having a plurality of frequency components to the object and receiving the ultrasonic waves reflected from the object or transmitted through the object; frequency component extracting means for extracting at least one frequency component from the detection signals; second image data generating means for generating second image data on the object based on intensity of the at least one frequency component extracted by the frequency component extracting means; and image selecting means for selecting at least one of the first image data generated by the first image data generating means and the second image data generated by the second image data generating means.

Further, an ultrasonic diagnosing apparatus according to a second aspect of the present invention includes: frequency component extracting means for extracting a plurality of frequency components from detection signals obtained by transmitting ultrasonic waves having a plurality of frequency components to an object to be inspected and receiving the ultrasonic waves reflected from the object or transmitted through the object; computing means for calculating relative relationship between intensity of the plurality of frequency components extracted by the frequency component extracting means; and image data generating means for generating image data on the object based on the relative relationship between intensity of the plurality of frequency components calculated by the computing means.

According to the present invention, the SN ratio can be improved and characteristic tissues can be emphatically displayed by acquiring information unique to tissues such as organs, bones, etc. in a living body based on intensity of at least one frequency component extracted by the frequency component extracting means.

BRIEF DESCRIPTION OF THE DRAWINGS

FIG. 6 is a block diagram showing the constitution of an ultrasonic diagnosing apparatus according to the second embodiment of the present invention.

DESCRIPTION OF THE PREFERRED EMBODIMENTS

Figure 1:
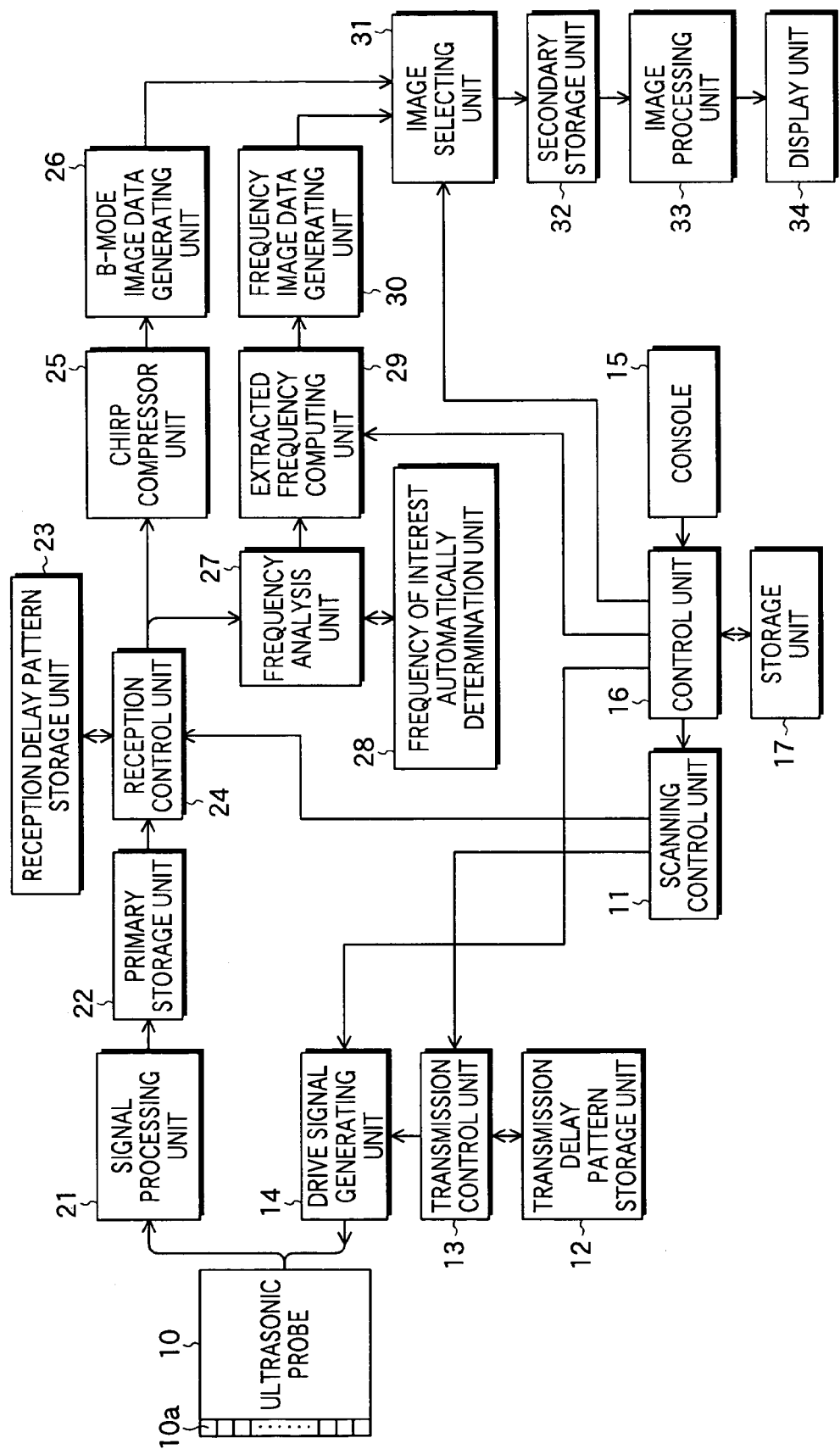
FIG. 1 is a block diagram showing the constitution of an ultrasonic diagnosing apparatus according to the first embodiment of the present invention.

Hereinafter, embodiments of the present invention will be described in detail by referring to the drawings. The same component elements are assigned with the same reference numbers and the description thereof will be omitted.

FIG. 1 is a block diagram showing the constitution of an ultrasonic diagnosing apparatus according to the first embodiment of the present invention. The ultrasonic diagnosing apparatus according to the embodiment includes an ultrasonic probe 10, a scanning control unit 11, a transmission delay pattern storage unit 12, a transmission control unit 13 and a drive signal generating unit 14.

The ultrasonic probe 10 to be used by being abutted on an object to be inspected includes plural ultrasonic transducers 10a arranged in a one-dimensional or two-dimensional manner that form a transducer array. These ultrasonic transducers 10a transmit ultrasonic beams based on applied drive signals, and receive propagating ultrasonic echoes to output detection signals.

Each ultrasonic transducer is constituted by a vibrator in which electrodes are formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like. When a voltage is applied to the electrodes of the vibrator by transmitting pulse electric signals or continuous wave electric signals, the piezoelectric material expands and contracts. By the expansion and contraction, pulse ultrasonic waves or continuous wave ultrasonic waves are generated from the respective vibrators, and an ultrasonic beam is formed by compounding these ultrasonic waves. Further, the respective vibrators expand and contract by receiving the propagating ultrasonic waves and generate electric signals. These electric signals are outputted as detection signals of ultrasonic waves.

Alternatively, as the ultrasonic transducers, plural kinds of elements of different conversion types may be used. For example, the above described vibrators are used as elements for transmitting ultrasonic waves and photo-detection type ultrasonic transducers are used as elements for receiving ultrasonic waves. The photo-detection type ultrasonic transducer is for detecting ultrasonic waves by converting ultrasonic signals into optical signals, and constituted by a Fabry-Perot resonator or fiber Bragg grating, for example.

Further, the ultrasonic waves transmitted through the object may be received by disposing an ultrasonic probe for transmitting ultrasonic waves and an ultrasonic probe for receiving ultrasonic waves to be opposed to each other. In this case, the distance between the probe for transmission and the probe for reception is made adjustable and these probes are used by abutting them against the object.

The scanning control unit 11 sets the transmission direction of ultrasonic beams and the reception direction of ultrasonic echoes sequentially. The transmission delay pattern storage unit 12 has stored plural transmission delay patterns to be used when ultrasonic beams are formed. The transmission control unit 13 selects one of the plural delay patterns stored in the transmission delay pattern storage unit 12 in accordance with the transmission direction set in the scanning control unit 11, and sets delay times to be provided to drive signals of the plural ultrasonic transducers 10a based on the delay pattern.

The drive signal generating unit 14 is constituted by a broadband signal generating circuit for generating broadband signals and plural drive circuits for providing desired delays to the broadband signals generated by the broadband signal generating circuit to generate plural drive signals to be supplied to the plural ultrasonic transducers 10a, respectively. These drive circuits delay the broadband signals based on the delay times set in the transmission control unit 13. In the embodiment, as the broadband signals, chirp signals, broadband burst signals, etc. having frequency components within a range of 0.5 MHz to 3.5 MHz are used, and, in transmission and reception of ultrasonic waves, broadband response characteristics of at least 0.5 MHz to 3.5 MHz are required. Note that, when the ultrasonic waves transmitted through the object are received, it is preferable to use broadband signals having frequency components within a range of 0.5 MHz to 2 MHz. Here, the "chirp signal" represents a signal the energy of which is dispersed in the timing axis direction by using a technology of signal conversion for changing the frequency timewise.

Further, the ultrasonic diagnosing apparatus according to the embodiment includes a console 15, a control unit 16 including a CPU, and a storage unit 17 such as a hard disk. The control unit 16 controls the scanning control unit 11, the drive signal generating unit 14, an extracted frequency computing unit 29, and an image selecting unit 31 based on the operation by the operator using the console 15. In the storage unit 17, there are stored programs for causing the CPU included in the control unit 16 to execute various kinds of operation, and frequency characteristics in transmission and reception of ultrasonic transducers.

Furthermore, the ultrasonic diagnosing apparatus according to the embodiment includes a signal processing unit 21, a primary storage unit 22, a reception delay pattern storage unit 23, a reception control unit 24, a chirp compressor unit 25, a B-mode image data generating unit 26, a frequency analysis unit 27, a frequency of interest automatically determination unit 28, the extracted frequency computing unit 29, a frequency image data generating unit 30, the image selecting unit 31, a secondary storage unit 32, an image processing unit 33, and a display unit 34.

In the signal processing unit 21, the detection signals outputted from the respective ultrasonic transducers 10a are amplified, subjected to attenuation correction due to distance by using an STC (sensitivity time control) amplifier, and converted into digital signals by A/D converters. As a sampling frequency of the A/D converter, at least about a tenfold frequency of the frequency of the ultrasonic wave is required, and a 16-fold or more frequency of the frequency of the ultrasonic wave is desirable. Further, as the resolution of the A/D converter, a resolution of ten or more bits is desirable.

The primary storage unit 22 stores the detection signals that have been converted into digital signals in the respective A/D converters of the signal processing unit 21 in chronological order for every ultrasonic transducer. The reception delay pattern storage unit 23 has stored plural reception delay patterns to be used when reception focusing process is performed on the plural detection signals outputted from the plural ultrasonic transducers 10a.

The reception control unit 24 selects one of the plural delay patterns stored in the reception delay pattern storage unit 23 in accordance with the reception direction set in the scanning control unit 11, provides delay times to the detection signals based on the selected pattern and adds the detection signals, thereby performs reception focusing process. Due to the reception focusing process, sound ray data is formed in which the focus of the ultrasonic echo is narrowed. The reception focusing process may be performed before the A/D conversion or the correction by the STC amplifier.

In the case where chirp signals are used as transmission waves, the chirp compressor unit 25 decodes sound ray data outputted from the reception control unit 24 by using the same chirp code used for encoding of the transmission waves, thereby performs processing of compressing information included in the plural frequency components within the broadband detection signals. Accordingly, in the case where burst signals are used as transmission waves, the chirp compressor unit 25 is unnecessary. The B-mode image data generating unit 26 generates B-mode image data by performing envelope detection processing on the decoded sound ray data outputted from the chirp compressor unit 25.

On the other hand, the frequency analysis unit 27 calculates plural frequency components included in the broadband detection signals from the sound ray data outputted from the reception control unit 24 by FFT (fast Fourier transform) with respect to each region in the depth direction of the object. The frequency of interest automatically determination unit 28 automatically determines at least one frequency component of interest from those frequency components. For example, the frequency of interest automatically determination unit 28 may determine a predetermined frequency component as the frequency component of interest, a frequency component having large intensity as the frequency component of interest, or a frequency component, at which frequency characteristic has a large peak or dip in the whole or a part of the region in the depth direction of the object, as the frequency component of interest.

Figure 2:
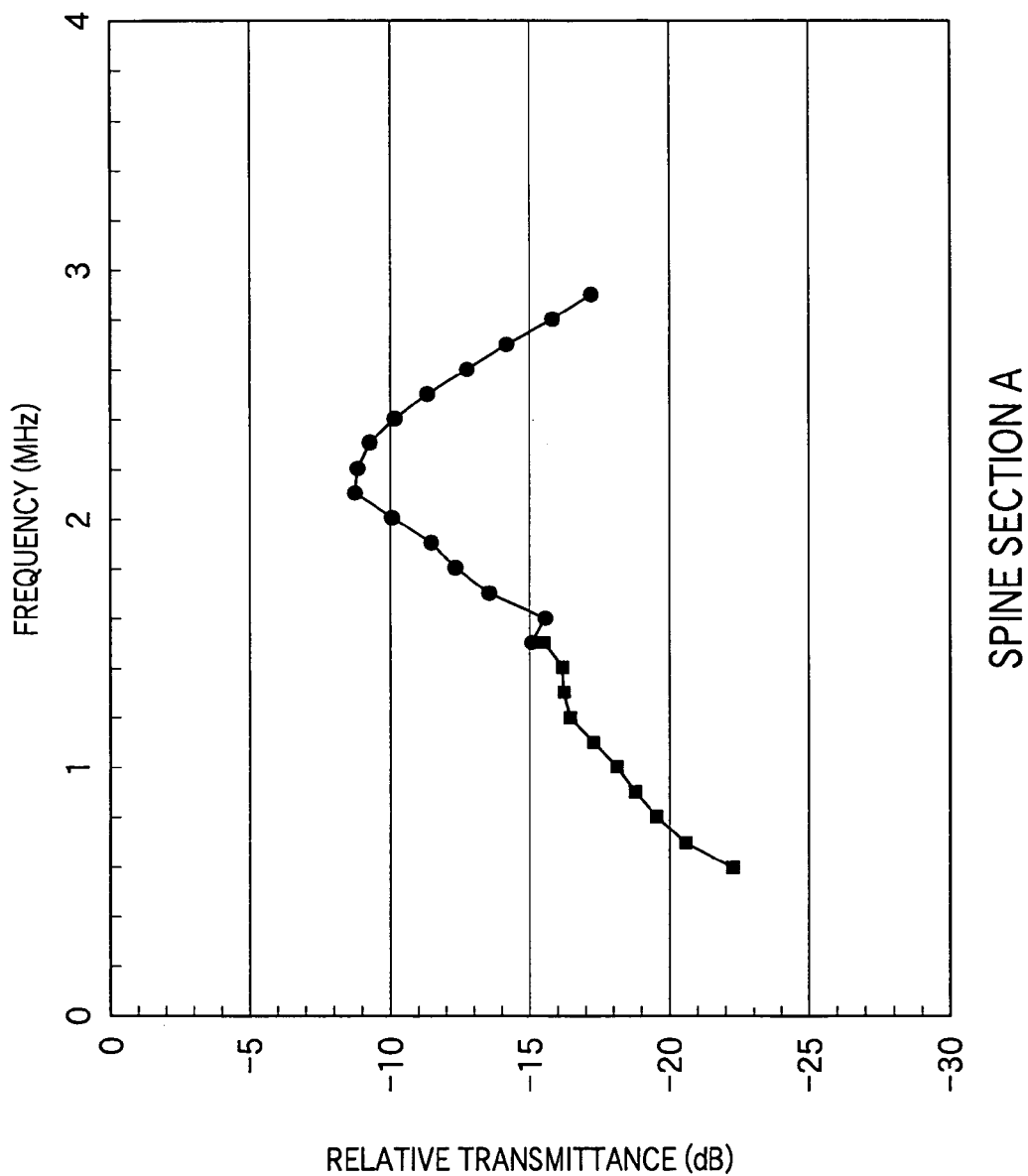
FIG. 2 shows frequency characteristics of relative transmittance in spine section A.
Figure 3:
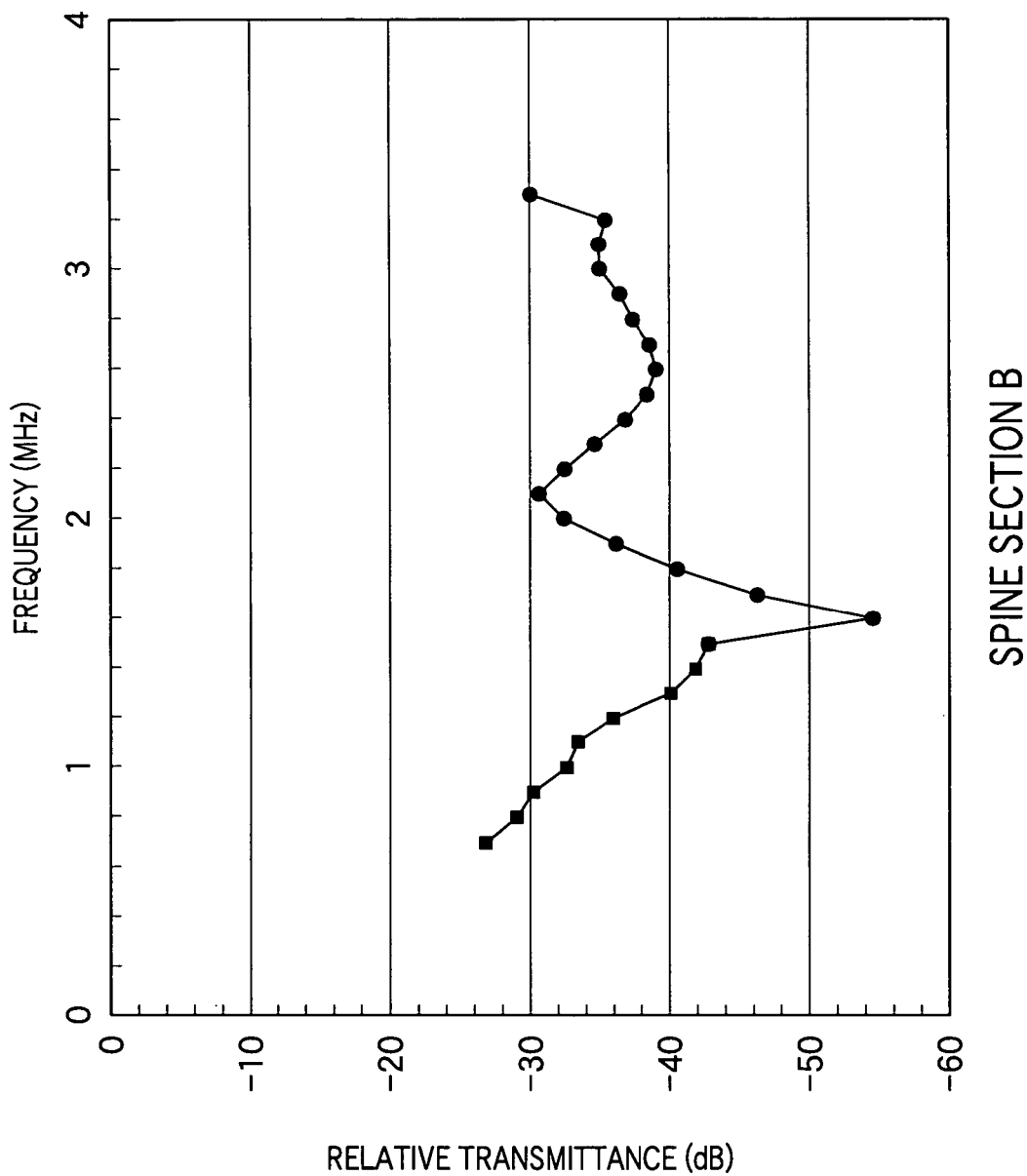
FIG. 3 shows frequency characteristics of relative transmittance in spine section B.
Figure 4:
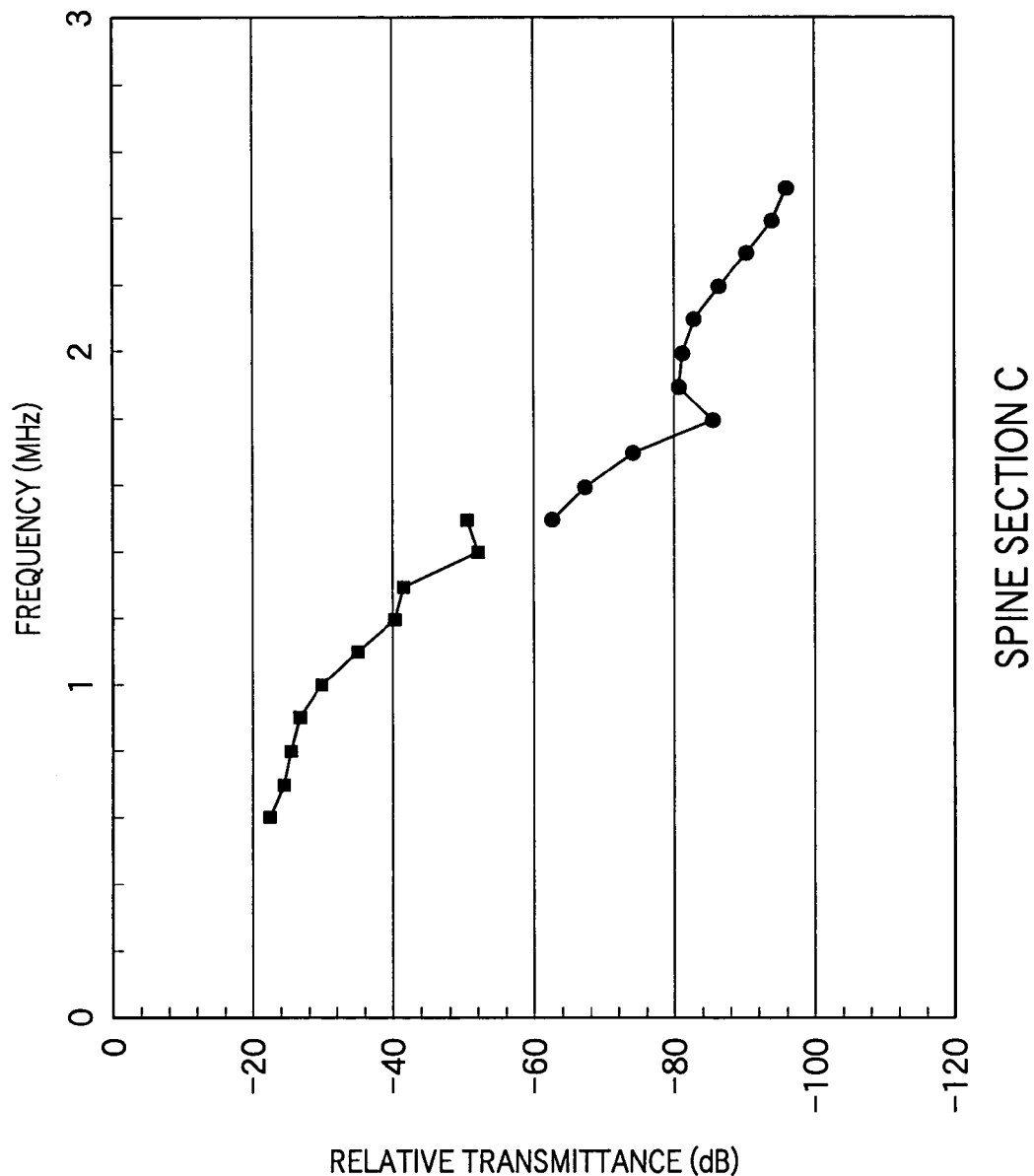
FIG. 4 shows frequency characteristics of relative transmittance in spine section C.

FIGS. 2-4 show differences in relative transmittance of ultrasonic waves depending on differences in tissues within the object. FIG. 2 shows frequency characteristics of relative transmittance in spine section A, FIG. 3 shows those in spine section B, and FIG. 4 shows those in spine section C. As the drive signals, chirp signals having a center frequency of 1 MHz and chirp signals having a center frequency of 2.25 MHz are used. Here, spine section A and spine section B are relatively soft tissues, but spine section C is a relatively hard tissue. As shown in FIGS. 2-4, the frequency characteristics of relative transmittance in the respective parts are largely different.

By determining frequency components based on the peculiarity on the frequency characteristics of a specific tissue in the part where ultrasonic echo intensity is large, the specific tissue can be displayed more emphatically. On the other hand, by determining frequency components while paying attention to the part where ultrasonic echo intensity is small, speckle components can be reduced which components are produced as a result of a large number of weak echoes being added to interfere. In either case, the SN ratio can be improved. Further, in the case where relative values of plural frequency components are calculated, a two-dimensional distribution of a specific tissue can be obtained accurately based on the relative values.

The extracted frequency computing unit 29 inputs at least one frequency component of interest, that has been determined by the frequency of interest automatically determination unit 28, from the frequency analysis unit 27, and performs correction of frequency characteristics in transmission and reception of ultrasonic transducers and so on. Here, if the frequency characteristics in transmission and reception of ultrasonic transducers have been stored in the storage unit 17, and the extracted frequency computing unit 29 corrects the intensity of the at least one frequency component, that has been inputted from the frequency analysis unit 27, based on the stored frequency characteristics of the ultrasonic transducers under control of the control unit 16, more accurate intensity can be obtained.

Furthermore, in the case where plural frequency components are inputted from the frequency analysis unit 27, the extracted frequency computing unit 29 may calculate relative relationship between intensity of the plural frequency components, for example, differences or ratios. Further, if not only the frequency components of the detection signals, but also phase components are extracted to be utilized for the generation of the ultrasonic images, even more information can be obtained. The frequency image data generating unit 30 generates frequency image data based on the data outputted from the extracted frequency computing unit 29.

The image selecting unit 31 selects one of the B-mode image data generated by the B-mode image data generating unit 26 and the frequency image data generated by the frequency image data generating unit 30, or compounds both images based on those image data. For example, the image selecting unit 31 may output luminance signals (or chromaticity signals) based on the B-mode image data generated by the B-mode image data generating unit 26, and chromaticity signals (or luminance signals) based on the frequency image data generated by the frequency image data generating unit 30.

The secondary storage unit 32 stores image data outputted from the image selecting unit 31. The image processing unit 33 performs various kinds of image processing on the image data that has been stored in the secondary storage unit 32. The display unit 34 includes a display device such as a CRT, an LCD, or the like, and displays an ultrasonic image based on the image data that has been subjected to image processing by the image processing unit 33.

Figure 5A:
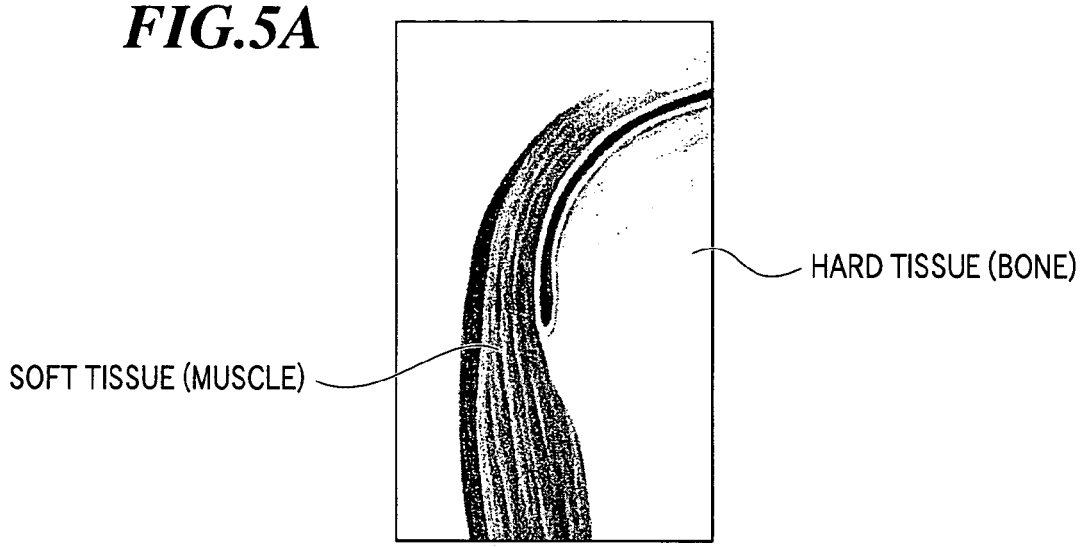
FIGS. 5A to 5C show examples of ultrasonic images displayed in the ultrasonic diagnosing apparatus according to the first embodiment of the present invention.
Figure 5B:
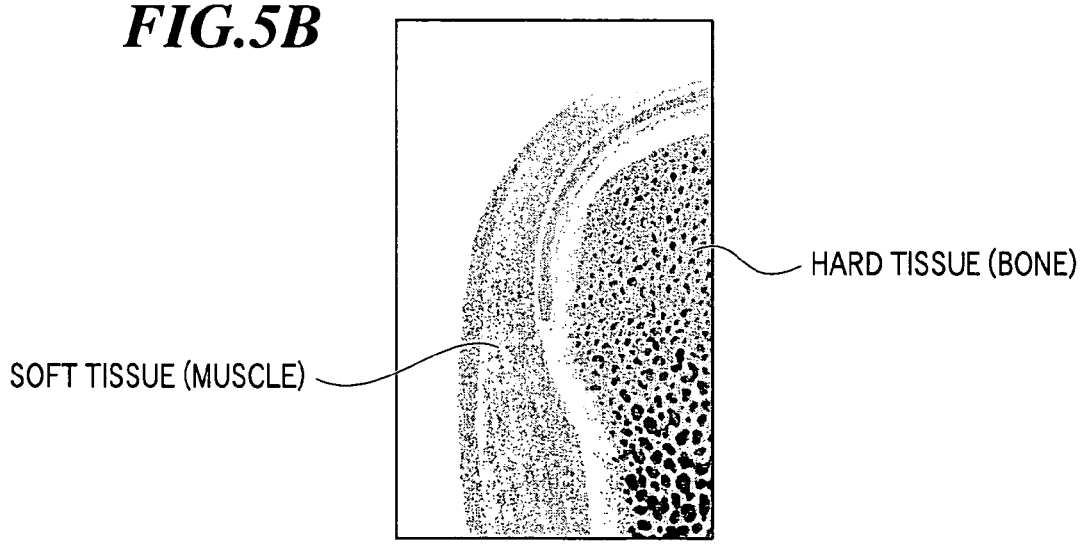
Figure 5C:
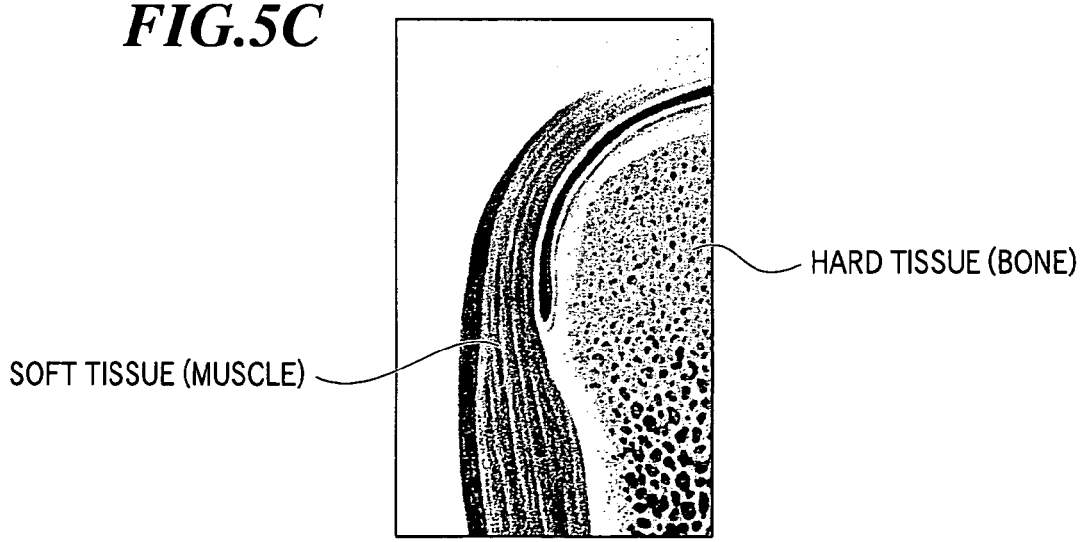

FIGS. 5A-5C schematically shows examples of ultrasonic images displayed in the ultrasonic diagnosing apparatus according to the embodiment. FIG. 5A shows a B-mode image. As shown in FIG. 5A, the ultrasonic image is generated in which the interior of the hard tissue (bone) is almost unclear, but the soft tissue (muscle) existing outside of the hard tissue (bone) is shown. On the other hand, FIG. 5B shows a frequency image. As shown in FIG. 5B, the interior of the hard tissue (bone) can be emphatically displayed by extracting suitable frequency components. Further, the separation of the hard tissue (bone) from the soft tissue (muscle) is clearly shown, and imaging from the bone to the skin can be performed. As shown in FIG. 5C, the B-mode image and the frequency image may be compounded to display a compounded image.

Next, the second embodiment of the present invention will be described.

FIG. 6 is a block diagram showing the constitution of an ultrasonic diagnosing apparatus according to the second embodiment of the present invention. According to this embodiment, the frequency of interest automatically determination unit 28 automatically determines plural frequency components of interest from frequency components calculated by the frequency analysis unit 27, the extracted frequency computing unit 29 calculates relative relationship between intensity of the determined frequency components, and the frequency image data generating unit 30 generates image data based on the relative relationship between intensity of the plural frequency components obtained by the extracted frequency computing unit 29. Further, in place of the image selecting unit 31 (FIG. 1) in the first embodiment, an image compounding unit 35 is provided. Other points are the same as in the first embodiment.

The frequency analysis unit 27 calculates plural frequency components included in the broadband detection signals from the sound ray data outputted from the reception control unit 24 by FFT with respect to each region in the depth direction of the object. The frequency of interest automatically determination unit 28 automatically determines plural frequency components of interest from those frequency components. For example, the frequency of interest automatically determination unit 28 may determine plural components respectively having predetermined frequencies as the plural frequency components of interest, plural frequency components having large intensity as the plural frequency components of interest, or plural frequency components having large peaks or dips in the whole or part of the regions in the depth direction of the object as the plural frequency components of interest.

The extracted frequency computing unit 29 inputs the plural frequency components of interest, that have been determined by the frequency of interest automatically determination unit 28, from the frequency analysis unit 27 and performs correction of frequency characteristics in transmission and reception of ultrasonic transducers and so on, and calculates relative relationship between intensity of the plural frequency components, for example, differences or ratios.

Specifically, in the case where the ratio of the intensity of one frequency component of 1.6MHz to another frequency component of 2MHz, which have been calculated by the frequency analysis unit 27, is −8 dB in spine section A, −24 dB in spine section B, and +14dB in spine section C, the extracted frequency computing unit 29 calculates the data corresponding to those values and outputs the calculated data. The frequency image data generating unit 30 generates frequency image data based on the data outputted from the extracted frequency computing unit 29.

In the case where image data is generated simply based on one frequency component, the image data is greatly affected by the intensity change of the frequency component. On the other hand, in the case where image data is generated based on the relative relationship between the plural frequency components as in this embodiment, the influence of the intensity changes of those frequency components is reduced, and image data reflecting the difference between frequency characteristics that represent the features of the tissue properties in the object can be generated.

The image compounding unit 35 compounds both images based on the B-mode image data generated by the B-mode image data generating unit 26 and the frequency image data generated by the frequency image data generating unit 30. For example, the image compounding unit 35 may output luminance signals (or chromaticity signals) based on the B-mode image data generated by the B-mode image data generating unit 26, and chromaticity signals (or luminance signals) based on the frequency image data generated by the frequency image data generating unit 30.

The secondary storage unit 32 stores image data outputted from the image compounding unit 35. The image processing unit 33 performs various kinds of image processing on the image data that has been stored in the secondary storage unit 32. The display unit 34 includes a display device such as a CRT, an LCD, or the like, and displays ultrasonic images based on the image data that has been subjected to image processing by the image processing unit 33.

The invention claimed is:

1. An ultrasonic diagnosing apparatus comprising:
   first image data generating means for generating first image data on an object to be inspected based on intensity of detection signals obtained by transmitting ultrasonic waves having a plurality of frequency components to the object and receiving the ultrasonic waves reflected from the object or transmitted through the object;
   frequency component extracting means for extracting at least one frequency component of interest from said detection signals based on a peculiarity of frequency characteristics of a specific tissue;
   second image data generating means for generating second image data on the object based on intensity of the at least one frequency component extracted by said frequency component extracting means; and
   image selecting means for selecting at least one of the first image data generated by said first image data generating means and the second image data generated by said second image data generating means.

2. The ultrasonic diagnosing apparatus according to claim 1, further comprising:
   transmitting means for transmitting ultrasonic waves having frequency components within a range of at least 0.5 MHz to 3.5 MHz.

3. The ultrasonic diagnosing apparatus according to claim 1, further comprising:
   storage means for storing frequency characteristics of a plurality of ultrasonic transducers to be used for transmission and/or reception of the ultrasonic waves; and
   computing means for correcting the intensity of the at least one frequency component extracted by said frequency component extracting means based on the frequency characteristics of said plurality of ultrasonic transducers stored in said storage means.

4. The ultrasonic diagnosing apparatus according to claim 1, wherein said frequency component extracting means includes:
frequency analysis unit for performing fast Fourier transform on each of said detection signals to obtain a plurality of frequency components; and
frequency determination unit for determining the at least one frequency component of interest to be extracted from among the plurality of frequency components obtained by said frequency analysis unit.

5. The ultrasonic diagnosing apparatus according to claim 4, wherein said frequency determination unit determines the at least one frequency component of interest, at which a frequency characteristic has a peak or a dip due to a difference between frequency characteristics of relative transmittance in respective parts of the object[1] from among the plurality of frequency components obtained by said frequency analysis unit.

6. The ultrasonic diagnosing apparatus according to claim 1, wherein said image selecting means compounds an image represented by the first image data generated by said first image data generating means and an image represented by the second image data generated by said second image data generating means and outputs image data representing a compounded image.

7. An ultrasonic diagnosing apparatus comprising:
frequency component extracting means for extracting a plurality of frequency components of interest from detection signals based on a peculiarity of frequency characteristics of a specific tissue, said detection signals obtained by transmitting ultrasonic waves having a plurality of frequency components to an object to be inspected and receiving the ultrasonic waves reflected from the object or transmitted through the object;
computing means for calculating relative relationship between intensity of the plurality of frequency components extracted by said frequency component extracting means; and
image data generating means for generating image data on the object based on the relative relationship between intensity of the plurality of frequency components calculated by said computing means.

8. The ultrasonic diagnosing apparatus according to claim 7, further comprising:
transmitting means for transmitting ultrasonic waves having frequency components within a range of at least 0.5 MHz to 3.5 MHz.

9. The ultrasonic diagnosing apparatus according to claim 7, further comprising:
storage means for storing frequency characteristics of a plurality of ultrasonic transducers to be used for transmission and/or reception of the ultrasonic waves;
wherein said computing means corrects the intensity of the plurality of frequency components extracted by said frequency component extracting means based on the frequency characteristics of said plurality of ultrasonic transducers stored in said storage means.

10. The ultrasonic diagnosing apparatus according to claim 7, wherein said frequency component extracting means includes:
frequency analysis unit for performing fast Fourier transform on each of said detection signals to obtain a plurality of frequency components; and
frequency determination unit for determining the plurality of frequency components of interest to be extracted from among the plurality of frequency components obtained by said frequency analysis unit.

11. The ultrasonic diagnosing apparatus according to claim 10, wherein said frequency determination unit determines the plurality of frequency components of interest, at which a frequency characteristic has peaks or dips due to a difference between frequency characteristics of relative transmittance in respective parts of the object, from among the plurality of frequency components obtained by said frequency analysis unit.

12. The ultrasonic diagnosing apparatus according to claim 7, further comprising:
second image data generating means for generating second image data on the object based on the intensity of said detection signals; and
image compounding means for compounding an image represented by the image data generated by said image data generating means and an image represented by the second image data generated by said second image data generating means and outputting image data representing a compounded image.

13. The ultrasonic diagnosing apparatus according to claim 1, further comprising:
a display unit that displays a first ultrasonic image based on the first image data when the first image data is selected by said image selecting means and a second ultrasonic image based on the second image data when the second image data is selected by said image selecting means.

* * * * *